United States Patent
Palovich et al.

(10) Patent No.: US 7,507,747 B2
(45) Date of Patent: Mar. 24, 2009

(54) MUSCARINIC ACETYLCHOLINE RECEPTOR ANTAGONISTS

(75) Inventors: Michael R. Palovich, King of Prussia, PA (US); Zehong Wan, King of Prussia, PA (US); Chongjie Zhu, King of Prussia, PA (US)

(73) Assignee: Glaxo Group Limited, Greenford, Middlesex (GB)

( * ) Notice: Subject to any disclaimer, the term of this patent is extended or adjusted under 35 U.S.C. 154(b) by 263 days.

(21) Appl. No.: 10/575,837

(22) PCT Filed: Oct. 15, 2004

(86) PCT No.: PCT/US2004/034234

§ 371 (c)(1), (2), (4) Date: Apr. 13, 2006

(87) PCT Pub. No.: WO2005/037224

PCT Pub. Date: Apr. 28, 2005

(65) Prior Publication Data

US 2007/0135478 A1    Jun. 14, 2007

Related U.S. Application Data

(60) Provisional application No. 60/512,161, filed on Oct. 17, 2003.

(51) Int. Cl.
- *A01N 43/42* (2006.01)
- *A61K 31/44* (2006.01)
- *C07D 451/02* (2006.01)
- *C07D 401/00* (2006.01)
- *C07D 405/00* (2006.01)
- *C07D 409/00* (2006.01)

(52) U.S. Cl. .................. 514/304; 546/124; 546/125

(58) Field of Classification Search ................ 546/124, 546/125; 514/304

See application file for complete search history.

(56) References Cited

U.S. PATENT DOCUMENTS

| | | | |
|---|---|---|---|
| 2,800,478 A | 7/1957 | Zirkle et al. | |
| 2,800,481 A | 7/1957 | Zirkle et al. | |
| 3,634,852 A | 1/1972 | Hartley et al. | |
| 4,826,838 A * | 5/1989 | Richardson et al. | 514/210.16 |
| 5,590,645 A | 1/1997 | Davies et al. | |
| 5,780,466 A | 7/1998 | Emonds-Alt et al. | |
| 5,860,419 A | 1/1999 | Davies et al. | |
| 5,873,360 A | 2/1999 | Davies et al. | |
| 6,248,752 B1 | 6/2001 | Smith | |
| 6,262,066 B1 | 7/2001 | Tulshian et al. | |
| 6,350,758 B1 | 2/2002 | Kozikowski et al. | |
| 6,455,527 B2 | 9/2002 | Tulshian et al. | |
| 6,696,462 B2 | 2/2004 | Eickmeier et al. | |
| 6,750,226 B2 | 6/2004 | Forner et al. | |
| 7,232,841 B2 | 6/2007 | Busch-Petersen et al. | |
| 7,276,521 B2 | 10/2007 | Busch-Petersen et al. | |
| 7,384,946 B2 | 6/2008 | Busch-Petersen et al. | |
| 2002/0115662 A1 | 8/2002 | Boyd et al. | |
| 2005/0020660 A1 | 1/2005 | Guyaux et al. | |
| 2005/0113417 A1 | 5/2005 | Mammen et al. | |
| 2005/0209272 A1 | 9/2005 | Fernandez et al. | |
| 2005/0277676 A1 | 12/2005 | Laine et al. | |
| 2006/0160844 A1 | 7/2006 | Belmonte et al. | |
| 2006/0178395 A1 | 8/2006 | Belmonte et al. | |
| 2006/0178396 A1 | 8/2006 | Belmonte et al. | |
| 2007/0129396 A1 | 6/2007 | Wan et al. | |
| 2007/0173646 A1 | 7/2007 | Laine et al. | |
| 2007/0179180 A1 | 8/2007 | Busch-Petersen et al. | |
| 2007/0179184 A1 | 8/2007 | Busch-Petersen et al. | |
| 2007/0185088 A1 | 8/2007 | Busch-Petersen et al. | |
| 2007/0185090 A1 | 8/2007 | Busch-Petersen et al. | |
| 2007/0185148 A1 | 8/2007 | Busch-Petersen et al. | |
| 2007/0185155 A1 | 8/2007 | Laine et al. | |
| 2007/0232599 A1 | 10/2007 | Palovich et al. | |
| 2007/0249664 A1 | 10/2007 | Laine et al. | |

FOREIGN PATENT DOCUMENTS

| | | |
|---|---|---|
| EP | 0069715 | 6/1982 |
| GB | 2064336 | 6/1981 |
| GB | 2129691 | 5/1984 |
| GB | 2169265 | 7/1986 |
| GB | 2178965 | 2/1987 |
| GB | 2242134 | 9/1991 |
| WO | 87/05213 | 9/1987 |
| WO | 2006/055503 | 5/2006 |
| WO | 2006/055553 | 5/2006 |
| WO | 2006/062883 | 6/2006 |
| WO | 2006/062931 | 6/2006 |
| WO | 2006/065755 | 6/2006 |
| WO | 2006/065788 | 6/2006 |
| WO | 2007/018508 | 2/2007 |
| WO | 2007/018514 | 2/2007 |

OTHER PUBLICATIONS

Cazzola et al., Pulmonary Pharmacology & Therapeutics (1998), 11(5/6), 381-392.*
Zhang, et al.; J. Med. Chem.; 2001; 44; 3937-3945.
Brown, *History and Basic Properties*, Humana Press, USA pp. 7-9 (1989).
Caulfield, *Pharmac. Ther.*, vol. 58 pp. 319-379 (1993).
Costello, et al., *American Journal of Physiology*, vol. 276 (5) pp. L709-L714 (1999).
Fryer and Jacoby, *Am J Respir Crit Care Med*, vol. 158 (5, pt 3) pp. 154-160 (1998).
Fryer et al., *Life Sci*, vol. 64 (6-7) pp. 449-455 (1999).

(Continued)

*Primary Examiner*—D. Margaret Seaman
*Assistant Examiner*—Niloofar Rahmani
(74) *Attorney, Agent, or Firm*—Dara L. Dinner; Theodore R. Furman; Charles M. Kinzig

(57) ABSTRACT

Muscarinic Acetylcholine Receptor Antagonists and methods of using them are provided.

28 Claims, No Drawings

OTHER PUBLICATIONS

Hedge, et al., *Life Sciences*, vol. 64 (6/7) pp. 419-428 (1999).

Ikeda, et al., *Naunyn-Schmiedeberg's Arch Pharmacol.*, vol. 366, pp. 97-103, (2002).

Minette, et al., *Journal of Applied Physiology*, vol. 67(6) pp. 2461-2465 (1989).

Oprins, et al., *Annals of the New York Academy of Sciences*, vol. 915 pp. 102-106 (2000).

Yu, et al., *Yaoxue Xuebao*, vol. 18(10) pp. 766-774 (1983), with translation.

Zhang, et al., *Yaoxue Xuebao*, vol. 20(10) pp. 752-758 (1985), with translation.

Pauwels et al., *Am. J. Respir. Crit. Care Med.*, vol. 163 pp. 1256-1276 (2001).

Ran, et al., *Yaoxue Xuebao*, vol. 19 (5) pp. 361-366 (1984), with translation.

Wu, et al., *Zhongguo Yaowu Huaxue Zazhi*, vol. 3(1) pp. 23-26 (1993), with translation.

Sarau, *Mol. Pharmacol.*, vol. 56 (3) p. 657-63 (1999).

Van Rossum, et al., *Arch. Int. Pharmacodyn.*, vol. 143 p. 299 (1963) Best Available Copy.

Zirkle, et al., *J Med Chem*, vol. 27 pp. 1269-1279 (1962).

Zirkle, et al., *J Med Chem*, vol. 27 pp. 1279-1285 (1962).

Zirkle, et al., *J Med Chem*, vol. 5 pp. 341-356 (1962).

Zhang, et al., *J Med Chem*, vol. 44 pp. 3937-3945 (2001).

U.S. Appl. No. 10/585,830, filed Jul. 12, 2006, Laine, et al.

U.S. Appl. No. 10/598,743, filed Sep. 11, 2006, Budzik, et al.

U.S. Appl. No. 10/598,750, filed Sep. 11, 2006, Jin, et al.

U.S. Appl. No. 10/599,717, filed Oct. 6, 2006, Laine, et al.

U.S. Appl. No. 11/570,981, filed Dec. 20, 2006, Cooper, et al.

U.S. Appl. No. 11/573,097, filed Feb. 2, 2007, Busch-Petersen, et al.

U.S. Appl. No. 11/573,099, filed Feb. 2, 2007, Busch-Petersen, et al.

U.S. Appl. No. 11/766,318, filed Jun. 21, 2007, Busch-Petersen, et al.

U.S. Appl. No. 11/766,371, filed Jun. 21, 2007, Busch-Petersen, et al.

U.S. Appl. No. 11/774,885, filed May 1, 2006, Wan, et al.

U.S. Appl. No. 11/578,000, filed Apr. 26, 2007, Busch-Petersen, et al.

U.S. Appl. No. 11/997,451, filed Jan. 31, 2008, Busch-Petersen, et al.

U.S. Appl. No. 11/977,466, filed Jan. 31, 2008, Busch-Petersen, et al.

U.S. Appl. No. 12/063,719, filed Feb. 13, 2008, Laine, et al.

* cited by examiner

MUSCARINIC ACETYLCHOLINE RECEPTOR ANTAGONISTS

This application claims the benefit of U.S. Provisional Application No. 60/512,161 filed Oct. 17, 2003.

FIELD OF THE INVENTION

This invention relates to novel derivatives of 8-azoniabicyclo[3,2,1]octanes, pharmaceutical compositions, processes for their preparation, and use thereof in treating $M_3$ muscarinic acetylcholine receptor mediated diseases.

BACKGROUND OF THE INVENTION

Acetylcholine released from cholinergic neurons in the peripheral and central nervous systems affects many different biological processes through interaction with two major classes of acetylcholine receptors—the nicotinic and the muscarinic acetylcholine receptors. Muscarinic acetylcholine receptors (mAChRs) belong to the superfamily of G-protein coupled receptors that have seven transmembrane domains. There are five subtypes of mAChRs, termed $M_1$-$M_5$, and each is the product of a distinct gene. Each of these five subtypes displays unique pharmacological properties. Muscarinic acetylcholine receptors are widely distributed in vertebrate organs, and these receptors can mediate both inhibitory and excitatory actions. For example, in smooth muscle found in the airways, bladder and gastrointestinal tract, $M_3$ mAChRs mediate contractile responses. For review, please see {Brown 1989 247 /id}.

Muscarinic acetylcholine receptor dysfunction has been noted in a variety of different pathophysiological states. For instance, in asthma and chronic obstructive pulmonary disease (COPD), inflammatory conditions lead to loss of inhibitory $M_2$ muscarinic acetylcholine autoreceptor function on parasympathetic nerves supplying the pulmonary smooth muscle, causing increased acetylcholine release following vagal nerve stimulation. This mAChR dysfunction results in airway hyperreactivity mediated by increased stimulation of $M_3$ mAChRs {Costello, Evans, et al. 1999 72 /id} {Minette, Lammers, et al. 1989 248 /id}. Similarly, inflammation of the gastrointestinal tract in inflammatory bowel disease (IBD) results in $M_3$ mAChR-mediated hypermotility {Oprins, Meijer, et al. 2000 245 /id}. Incontinence due to bladder hypercontractility has also been demonstrated to be mediated through increased stimulation of $M_3$ mAChRs {Hegde & Eglen 1999 251 /id}. Thus the identification of subtype-selective mAChR antagonists may be useful as therapeutics in these mAChR-mediated diseases.

Despite the large body of evidence supporting the use of anti-muscarinic receptor therapy for treatment of a variety of disease states, relatively few anti-muscarinic compounds are in use in the clinic. Thus, there remains a need for novel compounds that are capable of causing blockade at $M_3$ mAChRs. Conditions associated with an increase in stimulation of $M_3$ mAChRs, such as asthma, COPD, IBD and urinary incontinence would benefit by compounds that are inhibitors of mAChR binding.

SUMMARY OF THE INVENTION

This invention provides for a method of treating a muscarinic acetylcholine receptor (mAChR) mediated disease, wherein acetylcholine binds to an $M_3$ mAChR and which method comprises administering an effective amount of a compound of Formula (I) or Formula (II) or a pharmaceutically acceptable salt thereof.

This invention also relates to a method of inhibiting the binding of acetylcholine to its receptors in a mammal in need thereof which comprises administering to aforementioned mammal an effective amount of a compound of Formula (I) or Formula (II).

The present invention also provides for the novel compounds of Formula (I) or Formula (II), and pharmaceutical compositions comprising a compound of Formula (I) or Formula (II), and a pharmaceutical carrier or diluent.

Compounds of Formula (I) or Formula (II) useful in the present invention are represented by the structure:

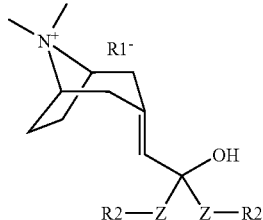

(I)

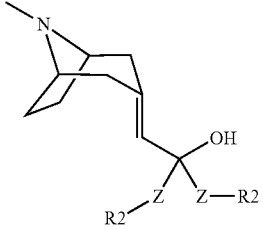

(II)

wherein:

$R1^-$ represents an anion associated with the positive charge of the N atom. $R1^-$ may be but is not limited to chloride, bromide, iodide, sulfate, benzene sulfonate and toluene sulfonate.

R2 is selected from the group consisting of cycloalkyl groups having from 5 to 6 carbon atoms, cycloalkyl-alkyl having 6 to 10 carbon atoms, heterocycloalkyl having 5 to 6 carbon atoms and N or O as the heteroatom, heterocycloalkyl-alkyl having 6 to 10 carbon atoms and N or O as the heteroatom, aryl, optionally substituted aryl, heteroaryl, and optionally substituted heteroaryl; and Z is a bond or ($C_1$-$C_6$)alkyl.

Suitable pharmaceutically acceptable salts are well known to those skilled in the art and include basic salts of inorganic and organic acids, such as hydrochloric acid, hydrobromic acid, sulphuric acid, phosphoric acid, methane sulphonic acid, ethane sulphonic acid, acetic acid, malic acid, tartaric acid, citric acid, lactic acid, oxalic acid, succinic acid, fumaric acid, maleic acid, benzoic acid, salicylic acid, phenylacetic acid and mandelic acid. In addition, pharmaceutically acceptable salts of compounds of Formula (I) or Formula (II) may also be formed with a pharmaceutically acceptable cation. Suitable pharmaceutically acceptable cations are well known to those skilled in the art and include alkaline, alkaline earth, ammonium and quaternary ammonium cations.

The following terms, as used herein, refer to:

"halo"—all halogens, that is chloro, fluoro, bromo and iodo.

"$C_{1-10}$alkyl" or "alkyl"—both straight and branched chain moieties of 1 to 10 carbon atoms, unless the chain length is otherwise limited, including, but not limited to, methyl, ethyl, n-propyl, iso-propyl, n-butyl, sec-butyl, iso-butyl, tert-butyl, n-pentyl and the like.

"cycloalkyl" is used herein to mean cyclic moiety, preferably of 3 to 8 carbons, including but not limited to cyclopropyl, cyclopentyl, cyclohexyl, and the like.

"alkenyl" is used herein at all occurrences to mean straight or branched chain moiety of 2-10 carbon atoms, unless the chain length is limited thereto, including, but not limited to ethenyl, 1-propenyl, 2-propenyl, 2-methyl-1-propenyl, 1-butenyl, 2-butenyl and the like.

"aryl"—phenyl and naphthyl;

"heteroaryl" (on its own or in any combination, such as "heteroaryloxy", or "heteroaryl alkyl")—a 5-10 membered aromatic ring system in which one or more rings contain one or more heteroatoms selected from the group consisting of N, O or S, such as, but not limited, to pyrrole, pyrazole, furan, thiophene, quinoline, isoquinoline, quinazolinyl, pyridine, pyrimidine, oxazole, tetrazole, thiazole, thiadiazole, triazole, imidazole, or benzimidazole.

"heterocyclic" (on its own or in any combination, such as "heterocyclicalkyl")—a saturated or partially unsaturated 4-10 membered ring system in which one or more rings contain one or more heteroatoms selected from the group consisting of N, O, or S; such as, but not limited to, pyrrolidine, piperidine, piperazine, morpholine, tetrahydropyran, thiomorpholine, or imidazolidine. Furthermore, sulfur may be optionally oxidized to the sulfone or the sulfoxide.

"arylalkyl" or "heteroarylalkyl" or "heterocyclicalkyl" is used herein to mean $C_{1-10}$ alkyl, as defined above, attached to an aryl, heteroaryl or heterocyclic moiety, as also defined herein, unless otherwise indicated.

Preferred compounds useful in the present invention include:
2-(8-Methyl-8-aza-bicyclo[3.2.1]oct-3-ylidene)-1,1-di-thiophen-2-yl-ethanol;
2-Benzyl-1-(8-methyl-8-aza-bicyclo[3.2.1]oct-3-ylidene)-3-phenyl-propan-2-ol;
2-(8-Methyl-8-aza-bicyclo[3.2.1]oct-3-ylidene)-1,1-diphenyl-ethanol;
3-(2-Hydroxy-2,2-di-thiophen-2-yl-ethylidene)-8,8-dimethyl-8-azonia-bicyclo[3.2.1]octane iodide;
3-(2-Benzyl-2-hydroxy-3-phenyl-propylidene)-8,8-dimethyl-8-azonia-bicyclo[3.2.1]octane iodide; and
3-(2-Hydroxy-2,2-diphenyl-ethylidene)-8,8-dimethyl-8-azonia-bicyclo[3.2.1]octane iodide.

More preferred compounds useful in the present invention include:
3-(2-Hydroxy-2,2-di-thiophen-2-yl-ethylidene)-8,8-dimethyl-8-azonia-bicyclo[3.2.1]octane iodide;
3-(2-Benzyl-2-hydroxy-3-phenyl-propylidene)-8,8-dimethyl-8-azonia-bicyclo[3.2.1]octane iodide; and
3-(2-Hydroxy-2,2-diphenyl-ethylidene)-8,8-dimethyl-8-azonia-bicyclo[3.2.1]octane iodide.

Methods of Preparation

Preparation

The compounds of Formula (I) and Formula (II) may be obtained by applying synthetic procedures, some of which are illustrated in the Schemes below. The synthesis provided for these Schemes is applicable for producing compounds of Formula (I) and Formula (II) having a variety of different R1 and R2 which are reacted, employing substituents which are suitable protected, to achieve compatibility with the reactions outlined herein. Subsequent deprotection, in those cases, then affords compounds of the nature generally disclosed. While some Schemes are shown with compounds only of Formula (II), this is merely for illustration purpose only.

The general preparation method is shown in Scheme I. The synthesis started with compound 1. Reaction with a suitable reagent R2-Z-M well known to those skilled in the art such as R2-Z-MgBr, R2-Z-Li and R2-Z-Zn$_{(1/2)}$ afforded alcohol 2, which was easily converted to quaternary ammonium salt 3 by reacting with appropriate reaction reagent (e.g., MeI and MeBr).

Scheme I.

A more specific preparation method leading to compound with Formula (I) and Formula (II) is outlined in Scheme II. Addition of PhCH$_2$MgBr to ester 1 furnished alcohol 4, which was easily converted to corresponding quarternary ammonium salt 5 by reacting with MeI.

Scheme II.

-continued

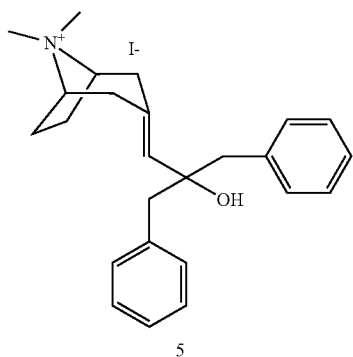

5

SYNTHETIC EXAMPLES

The following examples are provided as illustrative of the present invention but not limiting in any way:

Example 1

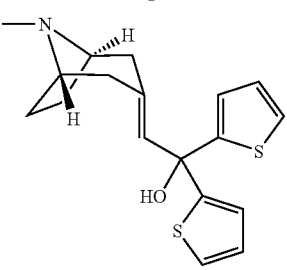

2-(8-Methyl-8-aza-bicyclo[3.2.1]oct-3-ylidene)-1,1-di-thiophen-2-yl-ethanol

A solution of (8-methyl-8-aza-bicyclo[3.2.1]oct-3-ylidene)-acetic acid methyl ester (200 mg, 1.02 mmol) in THF (3 mL) was mixed with 2-thienyllithium (2.02 mL, 1.0 M in THF, 2.02 mmol). The mixture was stirred overnight at r.t., diluted with saturated NH$_4$Cl aqueous solution (20 mL) and extracted with EtOAc. The combined organic phases were dried over MgSO$_4$ and concentrated. Flash chromatography (90% CH$_2$Cl$_2$, 8% CH$_3$OH, 2% NH$_4$OH) then afforded the title compound (132 mg, 39%): LCMS (ES) m/z 332 (M+H)$^+$; $^1$H-NMR(MeOD) δ 1.35 (m, 1H), 1.61 (m, 1H), 1.81 (m, 1H), 1.95 (m, 1H), 2.12 (m, 3H), 2.29 (s, 3H), 2.37 (m, 1H), 2.68 (m, 1H), 3.03 (m, 1H), 3.22 (m, 1H), 3.32 (s, 1H), 6.15 (s, 1H), 6.95 (m, 4H), 7.30 (m, 2H).

Example 2

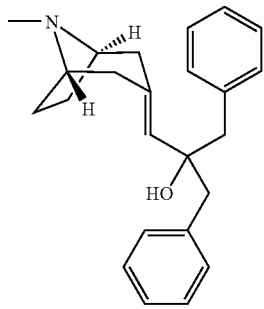

2-Benzyl-1-(8-methyl-8-aza-bicyclo[3.2.1]oct-3-ylidene)-3-phenyl-propan-2-ol

The title compound was prepared from (8-methyl-8-aza-bicyclo[3.2.1]oct-3-ylidene)-acetic acid methyl ester and benzylmagnesium chloride by following the experimental procedures in Example 1 (31% yield): LCMS (ES) m/z 348 (M+H)$^+$; $^1$H-NMR(CDCl$_3$) δ 0.90 (m, 1H), 1.25 (m, 1H), 1.61 (m, 1H), 1.81 (m, 3H), 2.20 (s, 3H), 2.40 (m, 1H), 2.70 (m, 1H), 2.87 (m, 1H), 2.97 (m, 2H), 3.08 (m, 1H), 3.42 (s, 2H), 5.24 (s, 1H), 7.26 (m, 10H).

Example 3

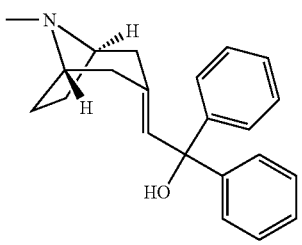

2-(8-Methyl-8-aza-bicyclo[3.2.1]oct-3-ylidene)-1,1-diphenyl-ethanol

The title compound was prepared from (8-methyl-8-aza-bicyclo[3.2.1]oct-3-ylidene)-acetic acid methyl ester and phenylmagnesium chloride by following the experimental procedures in Example 1 (44% yield): LCMS (ES) m/z 320 (M+H)$^+$; $^1$H-NMR(CDCl$_3$) δ 1.20 (m, 1H), 1.54 (m, 1H), 1.70 (m, 1H), 1.77 (m, 1H), 1.93 (m, 1H), 2.04 (m, 1H), 2.26 (s, 3H), 2.35 (m, 1H), 2.71 (m, 1H), 2.97 (m, 1H), 3.19 (m, 1H), 6.14 (s, 1H), 7.21 (m, 2H), 7.30 (m, 4H), 7.45 (m, 2H), 7.53 (m, 2H).

Example 4

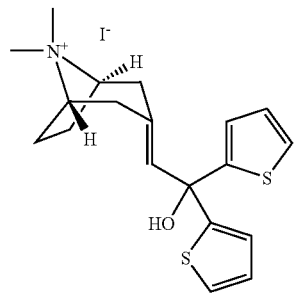

3-(2-Hydroxy-2,2-di-thiophen-2-yl-ethylidene)-8,8-dimethyl-8-azonia-bicyclo[3.2.1]octane iodide A solution of 2-(8-methyl-8-aza-bicyclo[3.2.1]oct-3-ylidene)-1,1-di-thiophen-2-yl-ethanol (10 mg, 0.03 mmol) in CH$_3$CN (1 mL) and CH$_2$Cl$_2$ (0.5 mL) was mixed with methyliodide (0.038 mL, 0.6 mmol) and K$_2$CO$_3$ (0.1 g, 0.7 mmol). The mixture was stirred overnight at r.t. and filtered. Separation via a reverse-phase HPLC then afforded the title compound (10 mg, 96%): LCMS (ES) m/z 346 (M+H)$^+$; $^1$H-NMR (CDCl$_3$) δ 1.28 (m, 1H), 2.04 (m, 2H), 2.29 (m, 2H), 2.51 (m, 2H), 2.64 (m, 1H), 3.30 (s, 6H), 4.07 (m, 1H), 4.38 (m, 1H), 5.93 (s, 1H), 6.62 (m, 1H), 6.85 (m, 1H), 6.98 (m, 1H), 7.03 (m, 1H), 7.11 (m, 1H), 7.46 (m, 1H).

Example 5

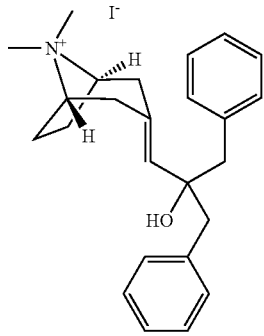

3-(2-Benzyl-2-hydroxy-3-phenyl-propylidene)-8,8-dimethyl-8-azonia-bicyclo[3.2.1]octane iodide The title compound was prepared from 2-benzyl-1-(8-methyl-8-aza-bicyclo[3.2.1]oct-3-ylidene)-3-phenyl-propan-2-ol and methyliodide by following the experimental procedures in Example 4 (85% yield): LCMS (ES) m/z 346 (M+H)$^+$; $^1$H-NMR(CDCl$_3$) δ 0.80 (m, 1H), 1.48 (m, 1H), 1.84 (m, 1H), 1.99 (m, 1H), 2.09 (m, 2H), 2.87 (m, 1H), 2.95 (m, 5H), 3.16 (s, 3H), 3.26 (s, 3H), 4.16 (m, 1H), 4.18 (m, 1H), 5.42 (s, 1H), 7.26 (m, 10H).

Example 6

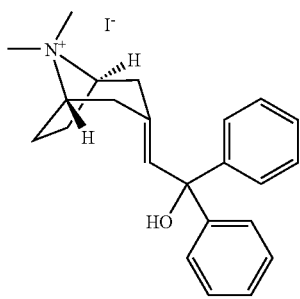

3-(2-Hydroxy-2,2-diphenyl-ethylidene)-8,8-dimethyl-8-azonia-bicyclo[3.2.1]octane iodide The title compound was prepared from 2-(8-methyl-8-azabicyclo[3.2.1]oct-3-ylidene)-1,1-diphenyl-ethanol and methyliodide by following the experimental procedures in Example 4 (67% yield): LCMS (ES) m/z 334 (M+H)$^+$; $^1$H-NMR(CDCl$_3$) δ 1.50 (m, 1H), 1.98 (m, 1H), 2.11 (m, 1H), 2.35 (m, 2H), 2.87 (m, 1H), 2.96 (m, 1H), 3.23 (m, 1H), 3.27 (s, 3H), 3.56 (s, 3H), 4.00 (m, 1H), 4.28 (m, 1H), 6.49 (s, 1H), 7.35 (m, 8H), 7.49 (m, 2H).

BIOLOGICAL EXAMPLES

The inhibitory effects of compounds at the M$_3$ mAChR of the present invention are determined by the following in vitro and in vivo assay:

Analysis of Inhibition of Receptor Activation by Calcium Mobilization:

Stimulation of mAChRs expressed on CHO cells were analyzed by monitoring receptor-activated calcium mobilization as previously described[10]. CHO cells stably expressing M$_3$ mAChRs were plated in 96 well black wall/clear bottom plates. After 18 to 24 hours, media was aspirated and replaced with 100 µl of load media (EMEM with Earl's salts, 0.1% RIA-grade BSA (Sigma, St. Louis Mo.), and 4 µM Fluo-3-acetoxymethyl ester fluorescent indicator dye (Fluo-3 AM, Molecular Probes, Eugene, OR) and incubated 1 hr at 37° C. The dye-containing media was then aspirated, replaced with fresh media (without Fluo-3 AM), and cells were incubated for 10 minutes at 37° C. Cells were then washed 3 times and incubated for 10 minutes at 37° C. in 100 µl of assay buffer (0.1% gelatin (Sigma), 120 mM NaCl, 4.6 mM KCl, 1 mM KH$_2$PO$_4$, 25 mM NaHCO$_3$, 1.0 mM CaCl$_2$, 1.1 mM MgCl$_2$, 11 mM glucose, 20 mM HEPES (pH 7.4)). 50 µl of compound ($1 \times 10^{-11}$-$1 \times 10^{-5}$ final in the assay) was added and the plates were incubated for 10 min. at 37° C. Plates were then placed into a fluorescent light intensity plate reader (FLIPR, Molecular Probes) where the dye loaded cells were exposed to excitation light (488 nm) from a 6 watt argon laser. Cells were activated by adding 50 µl of acetylcholine (0.1-10 nM final), prepared in buffer containing 0.1% BSA, at a rate of 50 µl/sec. Calcium mobilization, monitored as change in cytosolic calcium concentration, was measured as change in 566 nm emission intensity. The change in emission intensity is directly related to cytosolic calcium levels[11]. The emitted fluorescence from all 96 wells is measured simultaneously using a cooled CCD camera. Data points are collected every second. This data was then plotting and analyzed using GraphPad PRISM software.

Methacholine-Induced Bronchoconstriction Airway responsiveness to methacholine was determined in awake, unrestrained BalbC mice (n=6 each group). Barometric plethysmography was used to measure enhanced pause (Penh), a unitless measure that has been shown to correlate with the changes in airway resistance that occur during bronchial challenge with methacholine[12]. Mice were pretreated with 50 µl of compound (0.003-10 µg/mouse) in 50 µl of vehicle (10% DMSO) intranasally, and were then placed in the plethysmography chamber. Once in the chamber, the mice were allowed to equilibrate for 10 min before taking a baseline Penh measurement for 5 minutes. Mice were then challenged with an aerosol of methacholine (10 mg/ml) for 2 minutes. Penh was recorded continuously for 7 min starting at the inception of the methacholine aerosol, and continuing for 5 minutes afterward. Data for each mouse were analyzed and plotted by using GraphPad PRISM software.

All publications, including but not limited to patents and patent applications, cited in this specification are herein incorporated by reference as if each individual publication were specifically and individually indicated to be incorporated by reference herein as though fully set forth.

The above description fully discloses the invention including preferred embodiments thereof. Modifications and improvements of the embodiments specifically disclosed herein are within the scope of the following claims. Without further elaboration, it is believed that one skilled in the art can, using the preceding description, utilize the present invention to its fullest extent. Therefore the Examples herein are to be construed as merely illustrative and not a limitation of the scope of the present invention in any way. The embodiments of the invention in which an exclusive property or privilege is claimed are defined as follows.

What is claimed is:

1. A compound having structure I as indicated below:

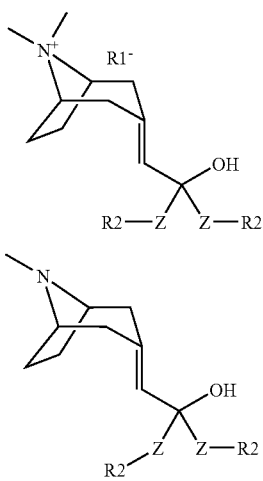

wherein:
R1⁻ represents a pharmaceutically acceptable anion associated with the positive charge of the N atom;
R2 is selected from the group consisting of cycloalkyl groups having from 5 to 6 carbon atoms, cycloalkyl-alkyl having 6 to 10 carbon atoms, heterocycloalkyl having 5 to 6 carbon atoms and N or O as the heteroatom, heterocycloalkyl-alkyl having 6 to 10 carbon atoms and N or O as the heteroatom, aryl, heteroaryl; and
Z is a bond or $(C_1-C_6)$alkyl.

2. A compound according to claim 1 wherein $R1^{31}$ is selected from the group consisting of chloride, bromide, iodide, sulfate, benzene sulfonate and toluene sulfonate.

3. A compound according to claim 1 selected from the group consisting of:
3-(2-Hydroxy-2,2-di-thiophen-2-yl-ethylidene)-8,8-dimethyl-8-azonia-bicyclo[3.2.1]octane iodide;
3-(2-Benzyl-2-hydroxy-3-phenyl-propylidene)-8,8-dimethyl-8-azonia-bicyclo[3.2.1]octane iodide; and
3-(2-Hydroxy-2,2-diphenyl-ethylidene)-8,8-dimethyl-8-azonia-bicyclo [3.2.1 ]octane iodide.

4. A pharmaceutical composition comprising a compound according to claim 1 and a pharmaceutically acceptable carrier thereof.

5. A compound according to claim 1 wherein R2 is heteroaryl.

6. A compound according to claim 5 wherein R2 is thienyl.

7. A compound according to claim 6 wherein Z is a bond.

8. A compound according to claim 1 wherein R2 is aryl.

9. A compound according to claim 8 wherein R2 is phenyl.

10. A compound according to claim 9 wherein Z is a $(C_1-C_6)$alkyl.

11. A compound according to claim 10 wherein Z is a $(C_1)$alkyl.

12. A compound according to claim 9 wherein Z is a bond.

13. A compound having structure II as indicated below:

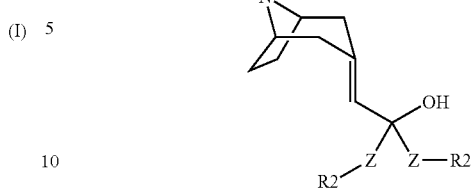

wherein:
R1⁻ represents a pharmaceutically acceptable anion associated with the positive charge of the N atom;
R2 is selected from the group consisting of cycloalkyl groups having from 5 to 6 carbon atoms, cycloalkyl-alkyl having 6 to 10 carbon atoms, heterocycloalkyl having 5 to 6 carbon atoms and N or O as the heteroatom, heterocycloalkyl-alkyl having 6 to 10 carbon atoms and N or O as the heteroatom, aryl and heteroaryl; and
Z is a bond or $(C_1-C_6)$alkyl.

14. A compound according to claim 12 wherein R1⁻ is selected from the group consisting of chloride, bromide, iodide, sulfate, benzene sulfonate and toluene sulfonate.

15. A compound according to claim 12 selected from the group consisting of:
2-(8-Methyl-8-aza-bicyclo[3.2.1]oct-3ylidene)-1,1-di-thiophen-2-yl-ethanol;
2-Benzyl-1-(8-methyl-8-aza-bicyclo[3.2.1]oct-3-ylidene)-3-phenyl-propan-2-ol; and
2-(8-Methyl-8-aza-bicyclo [3.2.1]oct-3-ylidene)-1,1-diphenyl-ethanol.

16. A compound according to claim 12 wherein R2 is heteroaryl.

17. A compound according to claim 16 wherein R2 is thienyl.

18. A compound according to claim 17 wherein Z is a bond.

19. A compound according to claim 1 wherein R2 is aryl.

20. A compound according to claim 19 wherein R2 is phenyl.

21. A compound according to claim 20 wherein Z is a $(C_1-C_6)$alkyl.

22. A compound according to claim 21 wherein Z is a $(C_1)$alkyl.

23. A compound according to claim 20 wherein Z is a bond.

24. A compound according to claim 12 wherein R1⁻ is selected from the group consisting of chloride, bromide, iodide, sulfate, phosphate, methanesulfonate, ethane sulfonate, acetate, malate, tartrate, citrate, lactate, oxalate, succinate, fumarate, maleate, benzoate, salicylate, phenyl acetate, and mandelate.

25. A pharmaceutical composition comprising a compound according to claim 12 and a pharmaceutically acceptable carrier thereof.

26. A pharmaceutical composition comprising a compound according to claim 15 and a pharmaceutically acceptable carrier thereof.

27. A pharmaceutical composition comprising a compound according to claim 3 and a pharmaceutically acceptable carrier thereof.

28. A compound according to claim 1 wherein R1⁻ is selected from the group consisting of chloride, bromide, iodide, sulfate, phosphate, methanesulfonate, ethane sulfonate, acetate, malate, tartrate, citrate, lactate, oxalate, succinate, fumarate, maleate, benzoate, salicylate, phenyl acetate, and mandelate.

* * * * *